United States Patent [19]
Löffler et al.

[11] Patent Number: 6,068,611
[45] Date of Patent: May 30, 2000

[54] CATHETER HAVING CENTERING MEANS

[75] Inventors: Edgar German Löffler, Kleve, Germany; Arie Luite Visscher, Driebergen, Netherlands

[73] Assignee: Delft Instruments Intellectual Property B.V., Delft, Netherlands

[21] Appl. No.: 09/214,311
[22] PCT Filed: Jul. 4, 1997
[86] PCT No.: PCT/NL97/00386
    § 371 Date: Mar. 3, 1999
    § 102(e) Date: Mar. 3, 1999
[87] PCT Pub. No.: WO98/01185
    PCT Pub. Date: Jan. 15, 1998

[30] Foreign Application Priority Data

Jul. 5, 1996 [NL] Netherlands ............ 1003529

[51] Int. Cl.[7] .................................. A61M 29/00
[52] U.S. Cl. ................ 604/101; 604/101; 606/192; 606/194
[58] Field of Search ............ 604/95–101; 606/194, 606/192

[56] References Cited

U.S. PATENT DOCUMENTS

| | | |
|---|---|---|
| 4,781,681 | 11/1988 | Sharrow et al. . |
| 5,306,250 | 4/1994 | March et al. . |
| 5,383,856 | 1/1995 | Bersin ..................... 604/101 |
| 5,395,333 | 3/1995 | Brill ....................... 604/101 |
| 5,501,667 | 3/1996 | Verduin, Jr. ............... 604/96 |
| 5,505,702 | 4/1996 | Arney ..................... 604/101 |
| 5,540,659 | 7/1996 | Teirstein ................. 604/104 |
| 5,556,389 | 9/1996 | Liprie . |
| 5,618,266 | 4/1997 | Liprie . |
| 5,643,171 | 7/1997 | Bradshaw et al. . |

FOREIGN PATENT DOCUMENTS 91 02 312  6/1992  Germany .

*Primary Examiner*—Wynn Wood Coggins
*Assistant Examiner*—Kevin C. Sirmons
*Attorney, Agent, or Firm*—Griffin, Butler, Whisenhunt & Szipl, LLP

[57] ABSTRACT

A catheter comprising an elongated tube having a first channel for the guiding of a radioactive element and a second channel for the passage of a guide wire for the catheter, in which the elongated tube is provided on its outer circumference near its distal end with temporarily activatable centering means, the centering means being surrounded by recanalization means, and the centering means comprising a plurality of elongated balloons which are inflatable by fluid fed through at least one third channel and, in operation, allow the recanalization means to expand to form an elongated body, with respect to which the first channel is centered.

11 Claims, 1 Drawing Sheet

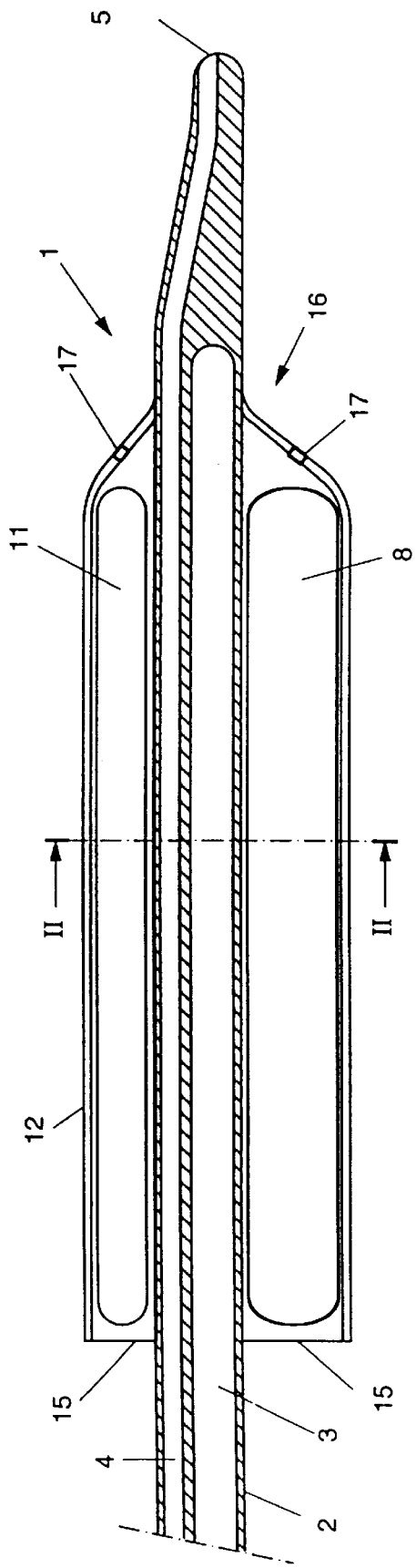
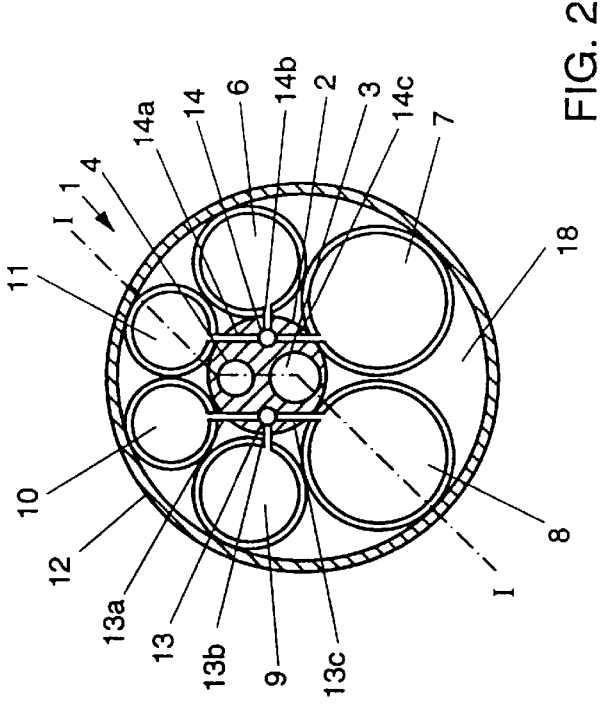

CATHETER HAVING CENTERING MEANS

The present invention relates to a catheter comprising an elongated tube having a first channel for the guiding of a radioactive element and a second channel for the passage of a guide wire for the catheter, the elongated tube being provided with temporarily activatable centering means on its outer circumference near its distal end.

BACKGROUND OF THE INVENTION

Such a catheter, known from EP-A-0 688 580, is intended for use after a recanalization treatment in which a substantially occluded blood vessel (for example as a result of the depositing of so-called plaque within the lumen of the blood vessel) is stretched by means of an expandable element, such as a fluid-inflatable recanalization balloon, fastened to the distal end of an elongated catheter tube, in order to permit the blood to flow unimpeded again through the stretched blood vessel.

It is frequently found after a relatively short period of time that a new recanalization treatment is necessary because a constriction is again forming in the blood vessel or has already formed. That constriction may be a consequence of tissue developing at the stretched place (known as neointima proliferation), probably due to the fact that the wall of the blood vessel is damaged by the stretching. This formation of tissue can be prevented to a large extent or at least reduced if, during or shortly after the recanalization treatment, the blood-vessel tissue in question is irradiated with ionizing radiation, in particular β and/or γ radiation.

For such a treatment, the catheter known from EP-A-0 668 580 can be used. The intensity of radiation of the radioactive element introduced decreases greatly with the distance. In order not to permit the radiation dose to be too great (damaging of vessel wall) or too low (not the intended reduction of tissue developing at the stretched place), it is important to center the radioactive element accurately in the blood vessel. This is done in the known catheter by centering means in the form of an inflatable balloon which is subdivided by constriction means into a plurality of balloon parts. The constriction means are so dimensioned that the different balloon parts communicate with each other.

Upon such a treatment, therefore, the recanalization catheter must first of all be brought to the desired place and, after the carrying out of the recanalization treatment, be removed and replaced by the catheter for the guiding of the radioactive element, in which connection, of course, great care must be paid to the fact that the radioactive element must be placed precisely at the place of the earlier recanalization treatment. All in all, this is a cumbersome and timeconsuming method which must be carried out with extreme caution, while, also from the standpoint of the patient who must undergo the treatment, it is preferable for it to be carried out as rapidly and efficiently as possible.

The object of the invention then is the provision of such an instrument that the treatment can be carried out in a short time and effectively and reliably with as few manipulations as possible.

SUMMARY OF THE INVENTION

This is achieved, in accordance with the invention, by a catheter of the type described above in that the centering means are surrounded by recanalization means, the centering means comprising a plurality of elongated balloons which are inflatable by a fluid introduced via a third channel and with respect to which the first channel is centered. By these measures, the recanalization treatment and the radiation treatment of the stretched region of the blood vessel can be carried out with one and the same catheter, in other words rapidly and without loss or time, since a catheter removal action and introduction action are avoided, which also is particularly valued by the patient. Furthermore, the fact that it is not necessary to change the catheter has the particular extra advantage that the centering means are automatically located at precisely the correct, desired place so that, in addition, there is also obtained a guarantee that the radiation will always be carried out at the correct place as well as in the correct manner.

The use of such a catheter for both the recanalization treatment and the radiation treatment results in a longer continuous dwell time of the catheter at the place of treatment than is the case upon use of two catheters introduced one after the other. In this connection, in accordance with a preferred embodiment of the invention, at least one perfusion channel is present which extends within the recanalization means and along the centering means from the proximal end of the recanalization means and the centering means to the distal end of the recanalization means and the centering means. By these measures the flow of the blood through the treated blood vessel can remain undisturbed to a far-reaching extent, which makes special measures with respect to this generally unnecessary.

BRIEF DESCRIPTION OF THE DRAWINGS

The invention will be described in further detail below with reference to the accompanying drawing.

FIG. 1 shows diagrammatically an example of a catheter in accordance with the invention on an enlarged scale, seen in longitudinal section along the line I—I of FIG. 2;

FIG. 2 shows diagrammatically a cross section through a catheter in accordance with the invention in the portion provided with centering means.

DESCRIPTION OF THE PREFERRED EMBODIMENTS

FIGS. 1 and 2 diagrammatically show, in longitudinal section and cross section respectively, an example of a distal end of a catheter 1 according to the invention, provided with centering means. The catheter shown comprises a tube 2 having a central channel 3 which in this example is closed at the distal end, and which serves to guide a radioactive radiation source to a predetermined place in a blood vessel in order to irradiate the wall of the blood vessel. The wall of the blood vessel has been or is stretched by recanalization means either previous to or concurrently with the irradiation. The catheter comprises a second lengthwise channel 4 for the passage of a guide wire for the catheter. The second lengthwise channel 4 is open at or near the distal end, as indicated at 5.

In this connection, it is pointed out that different techniques are known for the introduction of a balloon catheter into a blood vessel. As first technique, mention may be made of the so-called fixed-wire system, also known as the "on-the-wire system". A second technique is the socalled "over-the-wire" technique, in which the balloon catheter can be shoved over the guide wire and displaced. In accordance with a third technique, use is made of a balloon catheter, a relatively short segment of which is provided with a channel having an inlet and an outlet, the guide wire extending through this channel so that the catheter can be pushed along the guide wire. This last technique is generally referred to as the monorail system. This monorail system is also preferably, but not necessarily, used in catheters in accordance with the present invention. In the embodiment shown in FIG. 1, the channel 4 makes the catheter suitable for use of the monorail technique.

The catheter furthermore is provided with centering means and with recanalization means. The centering means comprise a plurality of elongated balloons 6, 7, 8, 9, 10, 11, arranged radially alongside each other around the tube 2, as can best be noted from FIG. 2. The balloons are fastened to the tube and can be inflated by one or more channels arranged in the tube. For this purpose a suitable fluid, which may be either a liquid or a gas or even a combination thereof, can be fed and later removed again via the channels.

For the feeding and removal of fluid to the balloons two channels 13, 14 are formed in the tube in the embodiment shown, which channels are in communication with the inside of the balloons through transverse channels 13a, 13b, 13c and 14a, 14b, 14c respectively.

The elongated balloons are located within recanalization means in a manner similar to that described in the related Dutch patent application NL 1003527 which recanalization means, however, in accordance with the present invention, do not consist of a closed balloon but of a sleeve 12 of supple material. The sleeve 12 can be connected with the outer surface of one or more or even all the balloons, but it can also be connected to the tube 2 by means of suitable connecting means 15, such as, for instance, strips or threads of a suitable material. The connecting means 15 can, for instance, be formed by, starting from an elongated balloon, removing parts of the balloon material at the ends. At the distal end, the connecting means, as shown in 16, can have a streamlined shape in order to avoid pushing up, and are provided with openings 17. The sleeve 12 can be viewed as an elongated balloon open at the front and rear.

The manner of operation of the catheter shown is as follows. First of all, the catheter is brought into a blood vessel by means of a guide wire in one of the manners known for this, until the part provided with the recanalization means is located at the place of a constriction which is to be treated. The elongated balloons 6 to and including 11 are then inflated via the channels 13 and 14. The balloons, via the sleeve 12, exert an outwardly directed force on the surrounding wall of the blood vessel, which is thereby somewhat stretched, due to which the constriction disappears. The sleeve limits the expansion of the balloons and furthermore has the result that the balloons center the channel 3 with respect to the sleeve, and therefore with respect to the wall of the blood vessel, Therefore, without further centering manipulations, a radioactive element can be pushed in the channel 3 in order to irradiate the wall of the blood vessel at the place of the constriction which was removed. Because the sleeve is open at its ends, and free spaces such as indicated at 18 are present between the balloons, the flow of blood through the blood vessel in question is not interrupted during the treatment.

It is pointed out that the centering manipulation should take place with respect to the channel 3 in which the radioactive element is present in operation. The channel 3 can, to be sure, be located in the center of the tube 2, but frequently this is not the case since the tube 2 also comprises still other channels. In the example shown, the channel 3 lies eccentrically in the tube. In order nevertheless to achieve a good centering, the balloons and/or the connecting means 15 should have a diameter or length respectively adapted to the radial position with respect to the tube. The diameter or length is greater as the balloons or connecting means are closer to the central channel 3. In FIG. 2 it can be seen that the balloons 7 and 8 have the largest diameter and the balloons 10 and 11 the smallest diameter.

It is furthermore pointed out that, on the basis of the foregoing, various modifications will be obvious to the person skilled in the art. One or more elongated balloons can, for instance, consist, as alternative, of a plurality of balloons arranged one behind the other. Furthermore, the sleeve can be constructed of a plurality of annular strips spaced apart from each other, which may or may not be connected to lengthwise strips.

Furthermore, the channel for the guide wire can be limited to the distal end of the catheter located past the centering means. The channel 4 then extends from the mouth 5 backwards to in front of the distal end of the centering means and there has an opening in the wall for the passage of the guide wire. The rest of the channel 4, which in FIG. 1 extends further in the direction of the proximal end, can then either be absent or be used in order to assume the function of one or both channels 13, 14. The connecting channels 13a, 13b, 13c and/or 14a, 14b, 14c are then of course connected to channel 4, and channels 13 and/or 14 are then superfluous.

We claim:

1. A catheter for recanalization and irradiation of an occluded blood vessel, comprising:
    (1) an elongated tube (2) having proximal and distal ends;
    (2) a first channel (3) in the tube (2) and being adapted to receive and guide a radioactive element near the distal end, said first channel having a closed distal end;
    (3) a second channel (4) in the tube (2) adapted to receive and pass therethrough a guidewire;
    (4) a centering means in the form of a plurality of fluid inflatable balloons (8) located on an outer periphery of the tube (2) near the distal end thereof such that when the balloons (8) are inflated the radioactive element is centered in the occluded blood vessel;
    (5) at least one third channel (13, 14) in the tube (2) for feeding an inflating fluid into the balloons (8); and
    (6) a recanalization means (12) surrounding the balloons (8) and being expandable by inflation of the balloons (8) to recanalize the occluded blood vessel.

2. A catheter according to claim 1, wherein, the recanalization means comprise a sleeve of supple material which lies around the elongated balloons and which is at least partly open at both ends.

3. A catheter according to claim 2, wherein the sleeve is connected to the tube by connecting means at least at its ends.

4. A catheter according to claim 3, wherein the sleeve and the connecting means have a smooth streamlined shape at the distal end.

5. A catheter according to claim 3, wherein the first channel is arranged eccentrically in the tube and diameters of the balloons are greater the closer the balloons are to the first channel.

6. A catheter according to claim 2, wherein the sleeve is fastened to an outer wall of one or more of the elongated balloons.

7. A catheter according to claim 1, wherein at least one perfusion channel extends within the recanalization means and along the centering means from a proximal end of the recanalization means and the centering means to a distal end of the recanalization means and the centering means.

8. A catheter according to claim 1, wherein, the elongated balloons are distributed radially around tube and that the free spaces present between the balloons form perfusion channels.

9. A catheter according to claim 1, wherein, characterized in that one or more of the elongated balloons are formed by a plurality of balloons placed one behind the other.

10. A catheter according to claim 1, wherein, characterized in that the second channel extends exclusively in the distal end of the tube extending in front of the recanalization and centering means.

11. The catheter of claim 1, wherein a diameter of the first channel is greater than a diameter of the second channel.

* * * * *